US010172569B2

(12) United States Patent
Seely et al.

(10) Patent No.: US 10,172,569 B2
(45) Date of Patent: Jan. 8, 2019

(54) SYSTEM AND METHOD FOR ASSISTING DECISIONS ASSOCIATED WITH EVENTS RELATIVE TO WITHDRAWAL OF LIFE-SUSTAINING THERAPY USING VARIABILITY MEASUREMENTS

(71) Applicant: Ottawa Hospital Research Institute, Ottawa (CA)

(72) Inventors: Andrew J. E. Seely, Ottawa (CA); Sonny Dhanani, Ottawa (CA); Nathan B. Scales, Ottawa (CA); Christophe L. Herry, Fournier (CA); Laura Hornby, Beaconsfield (CA); Timothy O. Ramsay, Ottawa (CA); Amanda S. Van Beinum, Ottawa (CA)

(73) Assignee: Ottawa Hospital Research Institute, Ottawa (CA)

( * ) Notice: Subject to any disclaimer, the term of this patent is extended or adjusted under 35 U.S.C. 154(b) by 104 days.

(21) Appl. No.: 15/259,330

(22) Filed: Sep. 8, 2016

(65) Prior Publication Data
US 2017/0071549 A1 Mar. 16, 2017

Related U.S. Application Data

(60) Provisional application No. 62/217,631, filed on Sep. 11, 2015.

(51) Int. Cl.
G06F 9/44 (2018.01)
A61B 5/00 (2006.01)
(Continued)

(52) U.S. Cl.
CPC .......... A61B 5/7275 (2013.01); A61B 5/0205 (2013.01); A61B 5/0456 (2013.01);
(Continued)

(58) Field of Classification Search
CPC .............................. A61B 5/7275; G16H 50/30
(Continued)

(56) References Cited

U.S. PATENT DOCUMENTS 7,542,912 B1 * 6/2009 Durand ................. G06F 19/322
705/2
RE41,236 E 4/2010 Seely
(Continued)

FOREIGN PATENT DOCUMENTS

WO 2007/142968 A2 12/2007
WO 2014/036651 A1 3/2014

OTHER PUBLICATIONS

Bradley, J.A. et al.; "Time to death after withdrawal of treatment in donation after circulatory death (DCD) donors"; Curr Opin Organ Transplant; vol. 18, No. 2; Apr. 2013; pp. 133-139.
(Continued)

Primary Examiner — Caleb Henry
(74) Attorney, Agent, or Firm — Brett J. Slaney; Blake, Cassels & Graydon LLP

(57) ABSTRACT

A system and method are provided that employ the variability of physiological waveforms to estimate the time to death after WLST, or time to inadequate organ perfusion. From the variability data one can derive an index subsequently used to determine the probability of death (or inadequate organ perfusion) within a given time frame in an automated fashion from bedside monitors in the intensive or post-anesthesia care unit. The resulting variability index can also be combined with the clinical variables used in other death prediction tools to enhance the performance and outcome when compared to existing models. In at least one implementation, variability monitoring at the bedside could be used to provide estimates of the probability that a patient will die within a certain time frame after WLST. These estimates could be used to reduce the distress of the patients'
(Continued)

families, as well as optimize the use of resources surrounding donation.

20 Claims, 14 Drawing Sheets

(51) Int. Cl.
*A61B 5/145* (2006.01)
*A61B 5/0205* (2006.01)
*A61B 5/0456* (2006.01)
*G06N 7/00* (2006.01)
*G06N 5/04* (2006.01)
*G16H 40/63* (2018.01)
*G16H 50/30* (2018.01)
*G16H 50/20* (2018.01)
*G06F 19/00* (2018.01)
*A61B 5/021* (2006.01)
*A61B 5/08* (2006.01)
*A61B 5/024* (2006.01)

(52) U.S. Cl.
CPC ........ *A61B 5/14542* (2013.01); *A61B 5/7203* (2013.01); *A61B 5/7264* (2013.01); *G06F 19/00* (2013.01); *G06N 5/045* (2013.01); *G06N 5/048* (2013.01); *G06N 7/005* (2013.01); *G16H 40/63* (2018.01); *G16H 50/20* (2018.01); *G16H 50/30* (2018.01); *A61B 5/021* (2013.01); *A61B 5/02405* (2013.01); *A61B 5/082* (2013.01)

(58) Field of Classification Search
USPC .......................................................... 706/52
See application file for complete search history.

(56) References Cited

U.S. PATENT DOCUMENTS

| | | | |
|---|---|---|---|
| 8,473,306 B2 | 6/2013 | Seely | |
| 2005/0159987 A1* | 7/2005 | Rosenfeld | G16H 50/20 705/3 |
| 2005/0177400 A1* | 8/2005 | Rosenfeld | G16H 50/20 705/3 |
| 2005/0187796 A1* | 8/2005 | Rosenfeld | G16H 50/20 705/3 |
| 2006/0271407 A1* | 11/2006 | Rosenfeld | A61B 5/412 705/3 |
| 2006/0271408 A1* | 11/2006 | Rosenfeld | G06F 19/325 705/3 |
| 2008/0001735 A1* | 1/2008 | Tran | G06F 19/3418 340/539.22 |
| 2008/0208618 A1* | 8/2008 | Schoenberg | G06F 19/3456 705/2 |
| 2013/0172691 A1* | 7/2013 | Tran | A61B 8/488 600/301 |
| 2014/0052473 A1* | 2/2014 | Stynchula | G16H 10/60 705/3 |
| 2015/0213202 A1* | 7/2015 | Amarasingham | G16H 50/30 705/2 |
| 2015/0213206 A1* | 7/2015 | Amarasingham | G06F 19/327 705/2 |
| 2015/0213207 A1* | 7/2015 | Amarasingham | G06F 19/327 705/2 |
| 2015/0213217 A1* | 7/2015 | Amarasingham | G16H 50/30 705/2 |
| 2015/0213222 A1* | 7/2015 | Amarasingham | G16H 50/30 705/2 |
| 2015/0213223 A1* | 7/2015 | Amarasingham | G16H 50/30 705/2 |
| 2015/0213224 A1* | 7/2015 | Amarasingham | G06F 19/3431 705/2 |
| 2015/0213225 A1* | 7/2015 | Amarasingham | G06F 19/3431 705/2 |

OTHER PUBLICATIONS

Munshi, L. et al.; "Predicting time to death after withdrawal of life-sustaining therapy"; Intensive Care Med; May 2015.

Bravi, A. et al. "Review and classification of variability analysis techniques with clinical applications"; Biomedical Engineering Online; 10:90; 2011.

Manuca, R. et al.; "Stationarity and nonstationarity in time series analysis"; Physica D; vol. 99; 1996; pp. 134-161.

Zhang, P.S. et al.; "Respiration Response Curve Analysis of Heart Rate Variability"; IEEE Transactions on Biomedical Engineering; vol. 44, No. 4; Apr. 1997; pp. 321-325.

Electrophysiology, Task Force of the European Society of Cardiology the North American Society of Pacing; "Heart sate Variability Standards of Measurement, Physiological Interpretation, and Clinical Use"; Circulation; vol. 93, Mar. 1996; pp. 1043-1065.

Cerutti, S. et al.; "Recent Advances in Heart Rate Variability Signal Processing and Interpretation"; IEEE Transactions on Biomedical Engineering; vol. 53, No. 1; Jan. 2006; pp. 1-3.

Goldman, J.M. et al.; "Neural network analysis of physiologic waveforms"; in Proceedings of the Annual International Conference of the IEEE Engineering in Medicine and Biology Society; vol. 13, No. 4; 199; pp. 1660-1661.

* cited by examiner

SYSTEM AND METHOD FOR ASSISTING DECISIONS ASSOCIATED WITH EVENTS RELATIVE TO WITHDRAWAL OF LIFE-SUSTAINING THERAPY USING VARIABILITY MEASUREMENTS

CROSS-REFERENCE TO RELATED APPLICATIONS

This application claims priority to U.S. Provisional Patent Application No. 62/217,631 filed on Sep. 11, 2015, the contents of which are incorporated herein by reference.

TECHNICAL FIELD

The following relates to systems and methods for assisting decisions associated with events relative to withdrawal of life-sustaining therapy using variability measurements.

DESCRIPTION OF THE RELATED ART

Many patients in the intensive care unit are provided with life-sustaining therapies. However, for some patients, the prognosis is deemed so poor that recovery is considered highly unlikely, and the life-sustaining therapies are withdrawn. Clinicians are typically unable to predict the time to death after the withdrawal of life-sustaining therapies (WLST), and a prolonged time to death can cause considerable distress for the patient as well as their families.

This inability to predict the time to death is especially relevant for potential organ donors after circulatory death. Because of functional warm ischemia, going beyond a certain point of time (e.g., up to 2 hours for lung and kidney, but less for liver) can irreversibly damage organs and preclude donation. As such, an accurate prediction of time to death after withdrawal of life sustaining therapy (WLST) is considered important in identifying appropriate donation after circulatory death (DCD) candidates, and in optimizing the use of resources surrounding donation. Presently, some data suggests that approximately 40% of potential DCD patients fail to die within acceptable limits of organ ischemia (e.g., 1-2 hours for most organs).

In some jurisdictions, the length of time that the transplant team is required to wait depends on both the functional warm ischemic time, defined as the time between the onset of inadequate organ perfusion until death, as well as the time from WLST until death. For example, in the UK, the cardiothoracic retrieval team and the abdominal team is meant to wait 2 and 3 hours, respectively, for the onset of functional warm ischemia (which, in their case, is defined as a systolic blood pressure of less than 50 mmHg). After this point, the patient needs to be deceased within 30 minutes to be able to donate a liver or pancreas, 1 hour for a lung donation, or 2 hours to donate kidneys, etc (Bradley et al, Curr Opin Organ Transplant 2013).

Therefore, it would be beneficial to both the families of the patient undergoing WLST as well as the organ transplant teams to be able to predict the time to death, the time to inadequate organ perfusion (when the blood pressure or oxygen saturation drops below a given threshold), and the functional warm ischemic time.

Several tools have been developed in the literature (see Shahin 2015) to identify patients that die within one hour after WLST, but have been found to not be widely used, most require external validation or were found to have poor performance in external validation studies. These tools are based on clinical variables such as physician opinion, pH, Glasgow Coma Scale, analgesia, positive end expiratory pressure, systolic blood pressure, vasopressor use, and so on.

SUMMARY

The following provides a system and method that employs the variability of physiological waveforms to assist decisions associated with events relative to, e.g., estimate the time to death after, WLST, or time to inadequate organ perfusion. From the variability data one can derive an index subsequently used to determine the probability or likelihood of death (or inadequate organ perfusion) within a given time frame in an automated fashion from bedside monitors in the intensive or post-anesthesia care unit. The resulting variability index can also be combined with the clinical variables used in other death prediction tools to enhance the performance and outcome when compared to existing models.

In at least one implementation, variability monitoring at the bedside could be used to provide estimates of the probability that a patient will die within a certain time frame after WLST. These estimates could be used to reduce the distress of the patients' families, as well as optimize the use of resources surrounding donation.

In one aspect, there is provided a method of assisting decisions associated with events relative to withdrawal of life sustaining therapy (WLST), the method comprising: obtaining one or more measures of variability from one or more organ systems; using the one or more measures of variability to generate a statistical model associated with an event relative to the WLST; and providing a clinical decision support indicator based on the event.

In other aspects, there are provided a computer readable medium comprising instructions for performing the above method and a system configured to perform the method.

BRIEF DESCRIPTION OF THE DRAWINGS

Embodiments will now be described by way of example only with reference to the appended drawings wherein.

DETAILED DESCRIPTION

Figure 1:
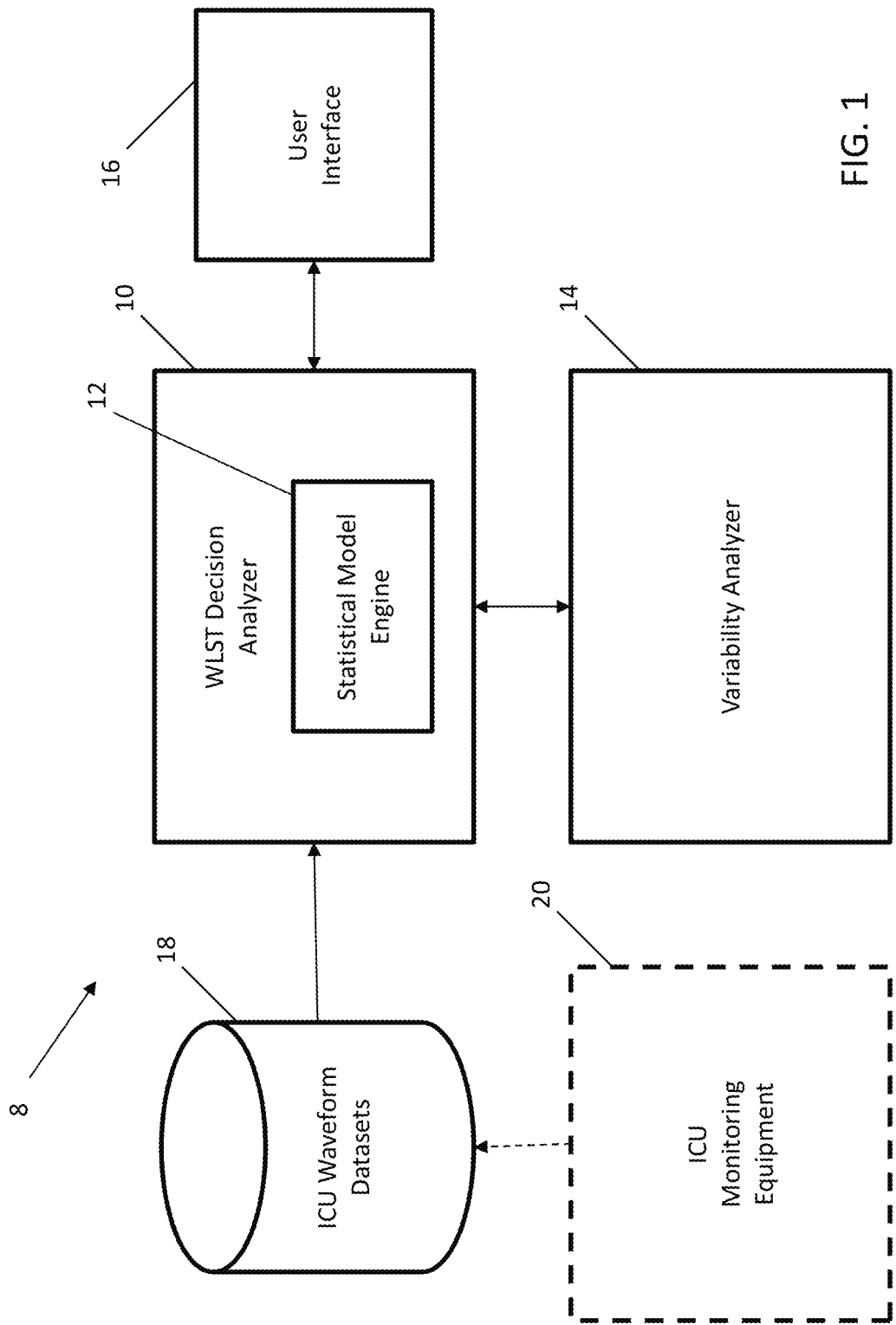
FIG. 1 is a block diagram of a system for providing variability decision support for WLST decision management.

It has been recognized that the variability of physiological waveforms can be employed to estimate the time to death after withdrawal of life sustaining therapy (WLST), and/or the time to inadequate organ perfusion. From the variability data one can derive an index subsequently used to determine the probability of death (or inadequate organ perfusion) within a given time frame in an automated fashion from bedside monitors in the intensive or post-anesthesia care unit. The resulting variability index can also be combined with the clinical variables used in, for example, other death prediction tools to enhance the use of such tools.

In at least one implementation, variability monitoring at the bedside could be used to provide estimates of the probability that a patient will die within a certain time frame after WLST. These estimates could be used to reduce the distress of the patients' families, as well as optimize the use of resources surrounding donation.

The following system and method employs continuous physiological waveform monitoring, and utilizes advanced analytics of patterns of variation (i.e. variability analyses) as well as available clinical information to classify a patient as likely to die within a given time frame after WLST.

The following system and method can also be used to provide an estimate of the probability or likelihood of death within this time.

The following system and method can also be used to employ continuous physiological waveform monitoring, variability analysis, and available clinical information to classify a patient as likely to have a time to inadequate organ perfusion less than a given threshold, and to provide an estimate of the probability of this time being less than the threshold.

The following system and method can also be used to employ continuous physiological waveform monitoring, variability analysis, and available clinical information to classify a patient as likely to have a functional warm ischemic time of less than a given period of time, and to provide an estimate of the probability that the functional warm ischemic time is less than this period.

The system described herein can therefore enable time to death and time to inadequate organ perfusion management to be improved, by providing clinicians with a system to support their decisions related to WLST. The system is based on the use of single or multi-organ variability, extracted from physiological waveforms acquired in ICUs. In particular, those waveforms undergo a phase of cleaning, event series extraction (e.g. R-R interval, inter-breath interval), and quality estimation (e.g., by applying techniques described in PCT Patent Application No. PCT/CA2013/050681 filed on Sep. 5, 2013 and entitled: "Method for Multi-Scale Quality Assessment for Variability Analysis", the contents of which are incorporated herein by reference and further details of which are provided below and shown in FIGS. 8 to 10). High quality event series may then be used to compute a variety of single-organ and multi-organ variability measures (e.g., see: Bravi, A., Longtin, A. & Seely, A. J. E. Review and classification of variability analysis techniques with clinical applications. *Biomedical Engineering Online* 10, (2011)), through a windowed analysis.

It will be appreciated that a "variability analysis over time" or a "variability analysis" in general, will hereinafter refer to the computation of a measure of variability for a plurality of time intervals for each patient parameter, variable, organ etc. Each measure of variability is indicative of a degree and character to which a respective patient parameter changes over an interval of time, and each variability analysis enables changes in variability of the patient parameter to be observed over a period of time. A variability analysis as herein described can be performed on one or more patient parameters, i.e. single parameter and/or multi-parameter (e.g. single-organ or multi-organ), and the multiple measures of variability can be obtained according to any suitable pattern such as intermittent, continuous, etc.

WLST Decision Management

The presently described system and method is adapted to integrate such variability measures with or without additional clinical information, to provide patient-specific indices related to:

1) predicting whether a patient will die within a given period of time after WLST;

2) the probability or likelihood of death within a given period of time after WLST;

3) predicting whether a patient's systolic, mean, or diastolic blood pressure or oxygen saturation will drop below a given threshold after a given period of time after WLST;

4) the probability or likelihood that a patient's systolic, mean, or diastolic blood pressure or oxygen saturation will drop below a given threshold after a given period of time after WLST;

5) predicting whether a patient's functional warm ischemic time remains less than a given threshold; and 6) the probability or likelihood that a patient's functional warm ischemic time remains less than a given threshold.

That is, the method described herein integrates variability measures such that when WLST occurs, clinically relevant information can be presented in order to enable clinical decisions to be made with respect to any one or more of the above predictions or probabilities.

The ability to provide indices for conveying the clinically relevant information, for a new patient, can be based on statistical models created using previously collected data from patients just prior to or immediately after WLST. The presented statistical models can be based on univariate linear support vector machines for simplicity, but may also include other types of generalized linear models, fuzzy c-means clustering, artificial neural network, multilayer perceptron, radial basis function network, support vector machines, decision trees, random forests, and Bayesian classifiers, as well as other types of ensembles, such as boosting, adaptive boosting and bagging. The clinically relevant variables used by the models are selected through optimization methods, such as brute force, grid search, greedy algorithms, Monte-Carlo methods, genetic algorithms, ant colony optimization. Cross-validation procedures such as leave-one-out, k-fold cross validation, and random resampling are used in combination with optimization methods for the identification of the models and their parameters.

It can be appreciated that the measures of variability in this context can also be used to assess how a patient has died. That is, the etiology, or the manner of dying, which is relevant to organ donation, can assist in presenting strategies for organ donation after cardiac death, and assist in determining therapeutic options to be administered.

Turning now to FIG. 1, a system 8 is shown, which includes a WLST decision analyzer 10. The analyzer 10 includes or otherwise has access to a statistical model engine 12 for generating and selecting from statistical models and for performing other modelling operations. The analyzer 10 also includes or has access to a variability analyzer 14, which may be located remotely therefrom. It can be appreciated that the analyzer 10 may be communicable with multiple variability analyzers 14. A user interface 16 is also shown, which enables inputs to be received, and outputs to be provided by, the analyzer 10. The user interface 16 may include any one or more input/output mechanisms and may present a graphical user interface, e.g., via a browser. It can be appreciated that the analyzers 10, 14 and user interface 16 may be implemented by or provided on any suitable electronic device, including desktop and laptop computers, smart phones, tablets, consoles, integrated into in-clinic or in-hospital monitoring systems, etc.

The analyzer 10 also includes or has access to an ICU waveform dataset database 18 storing waveform data utilized by the system 8. The ICU waveform datasets in the database 18 may originate from various sources, including ICU-based monitoring equipment 20, which may also be included in or be accessible to the system 8 (as illustrated in dashed lines). It can be appreciated that various platforms and architectures may be employed, including local and wide area network, open and closed systems, local and cloud-based storage and processing, etc.

Figure 2:
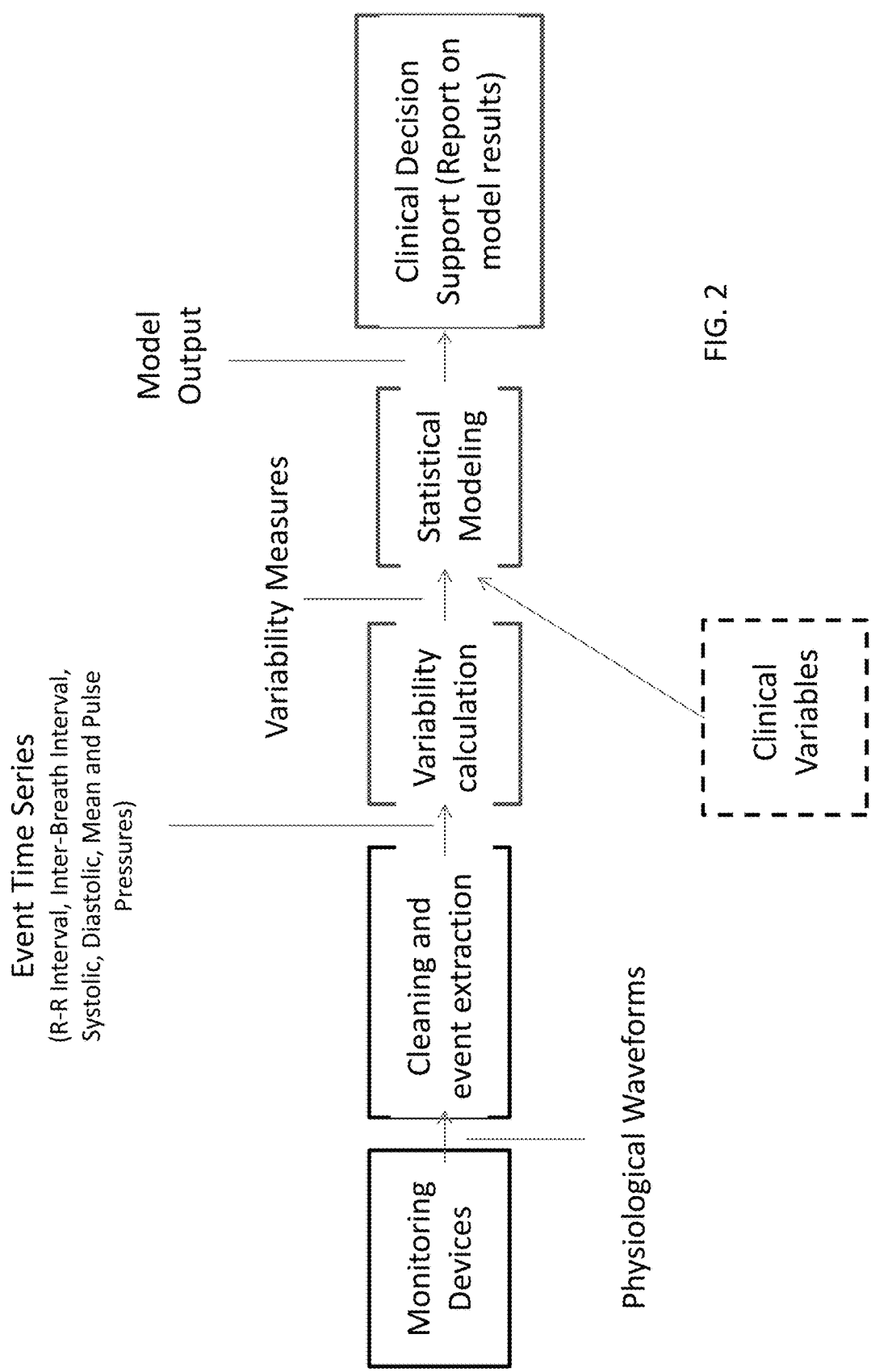
FIG. 2 is a flow diagram illustrating the generation of clinical decision support using variability measures.
Figure 3:
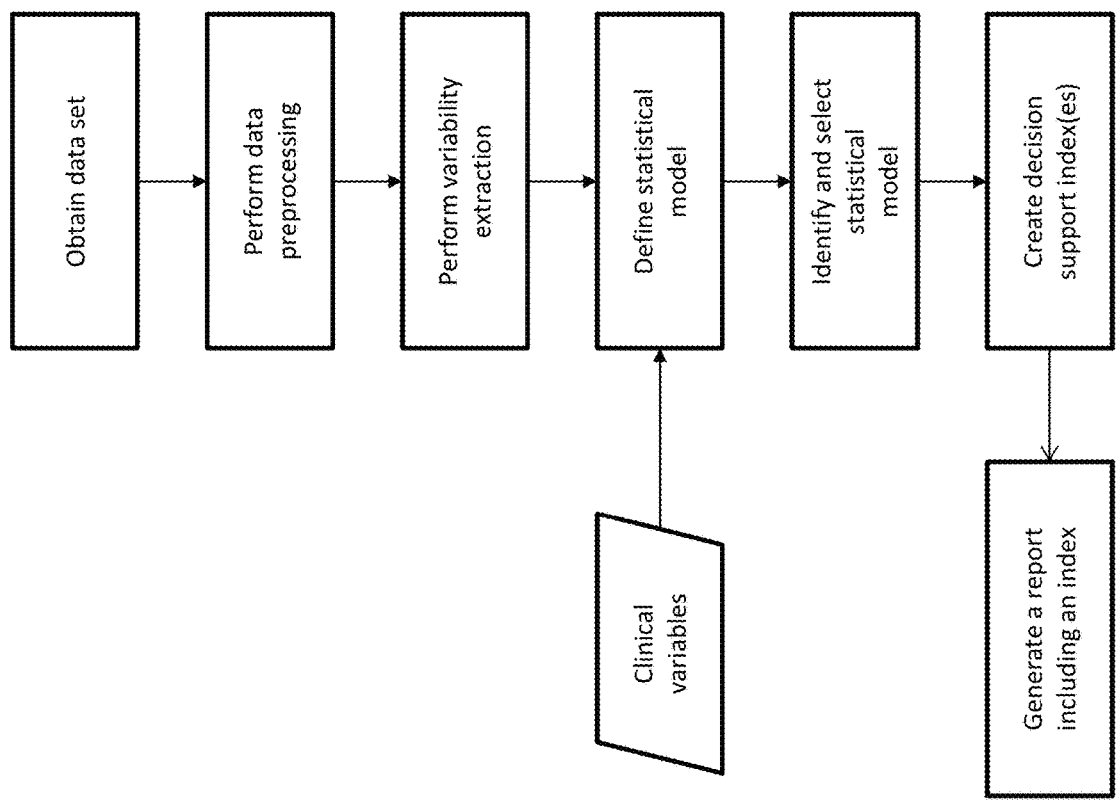
FIG. 3 is a flow chart illustrating computing executable instructions for generating clinical decision support using variability measures.

FIGS. 2 and 3 illustrate functional blocks and example computer executable operations respectively, that may be performed in providing multi-organ variability decision support for WLST management, as will now be described.

As shown in FIG. 2, monitoring devices produce physiological waveforms that are cleaned and events are extracted therefrom to produce one or more event time series. From these event time series, variability calculations are performed to generate variability measures that undergo statistical modeling. The statistical modeling can be optionally performed using clinical variables, depending on the application or scenario. The statistical modeling generates a model output, which can then be used to provide clinical decision support, e.g. by providing a report on the model results.

Dataset

The proposed system for the prediction of death or time to inadequate organ perfusion, within a given time frame, is based on a corresponding predictive model trained through a dataset including electrocardiographic, capnograph, and arterial blood pressure waveforms recorded from ICU patients immediately prior to and/or after the withdrawal of life sustaining therapies (WLSTs).

Data Preprocessing

After cleaning the electrocardiograms (EKGs), capnograms (expCO2), and arterial blood pressure waveforms (ABP) from artifacts (e.g., as described below), several different event time series are created: 1) the time elapsed between two successive R peaks of an EKG, and 2) the time elapsed between two successive expirations from an expCO2, 3) the time series of systolic, diastolic, mean, and pulse pressures.

Variability Extraction

From the event time series, a set of measures of heart rate variability (HRV), respiratory rate variability (RRV), and blood pressure variability (BPV) are extracted and tracked over time through a windowed analysis (using either a fixed time duration or a fixed number of samples). Then, the median value for each measure of variability is computed using a region of time prior to (and/or immediately after) WLST.

Statistical Model Definition

Patients will be classified into two groups (fast and slow) based on time to death less than or greater than X hours, where X is a predefined period of time of clinical interest (30 minutes, 1 hour, 2 hours, etc.) The set of variability measures are used as input features for a clinical prediction tool to predict the likelihood of a patient dying within this period. Different prediction strategies can be considered, such as decision trees, logistic regression and ensemble methods, with optimal prediction strategies determined based on Area under the Receiver Operating Characteristic curve (ROC-AUC), as well as the sensitivity, specificity and likelihood ratio metrics as indicators of performance of the predictive model, with, for example, 95% confidence intervals. The resulting model will therefore predict the likelihood that a given patient will die within X hours after WLST.

As an example, a univariate logistic regression model could be developed for each variability measure, with an output between 0 and 1, reflecting the risk of a patient dying within the chosen timeframe X (e.g. predetermined clinically). An ensemble of these univariate logistic regression models could then be built, using the average of the output of each individual model to determine an estimate of the overall risk that a given patient will die within the timeframe X. This output could be used as the score of the WLST Decision Analyzer 10.

As a simple example, if the model using variable i resulted in a probability p(i) that the patient would die with the chosen timeframe X, then the score for n combined models could be calculated as $p_n = (\Sigma p(i))/n$, where the sum runs from i=1 to n.

Figure 4:
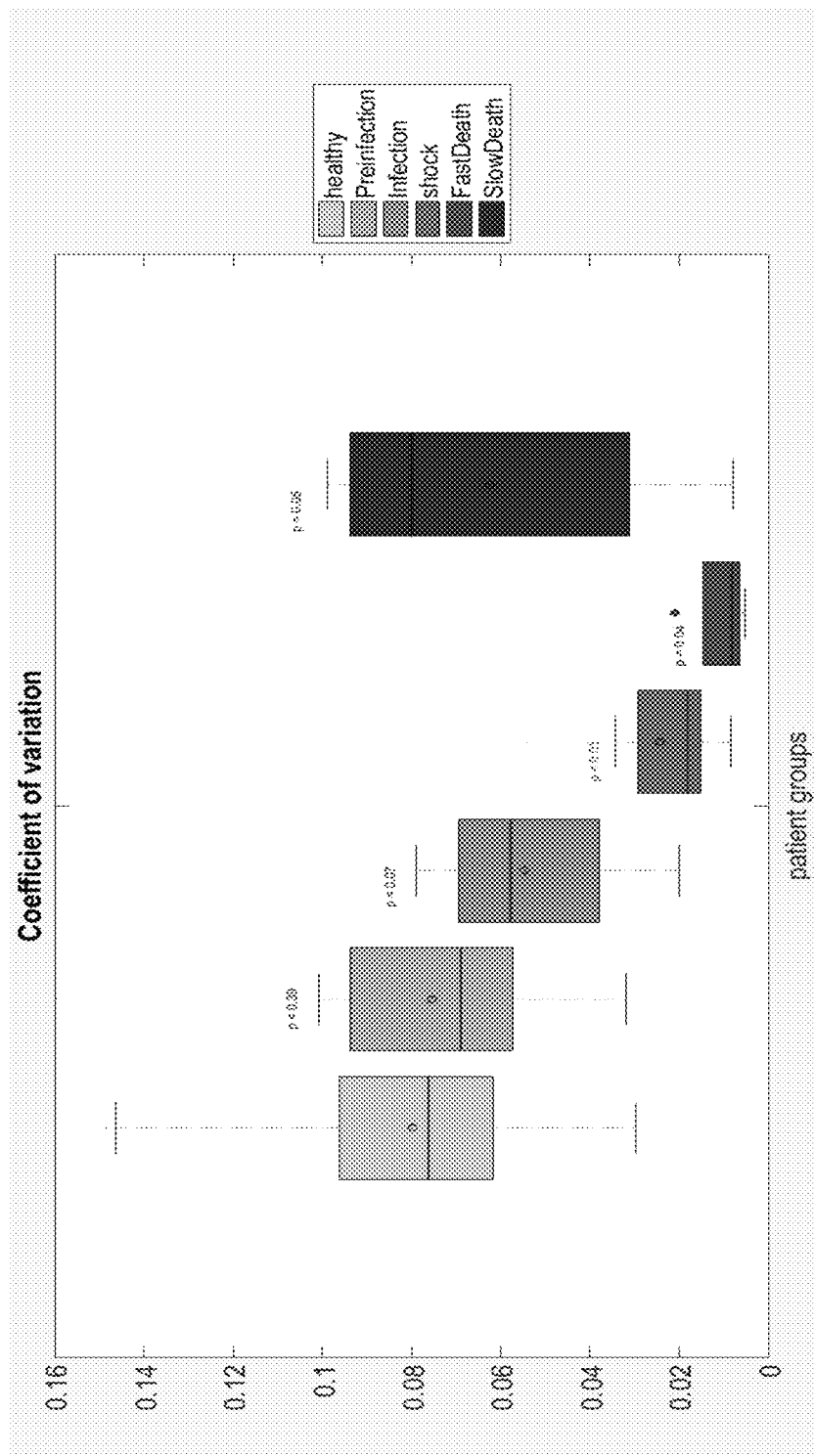
FIG. 4 is a chart illustrating coefficient of variation variability measures for a set of patient groups.
Figure 5:
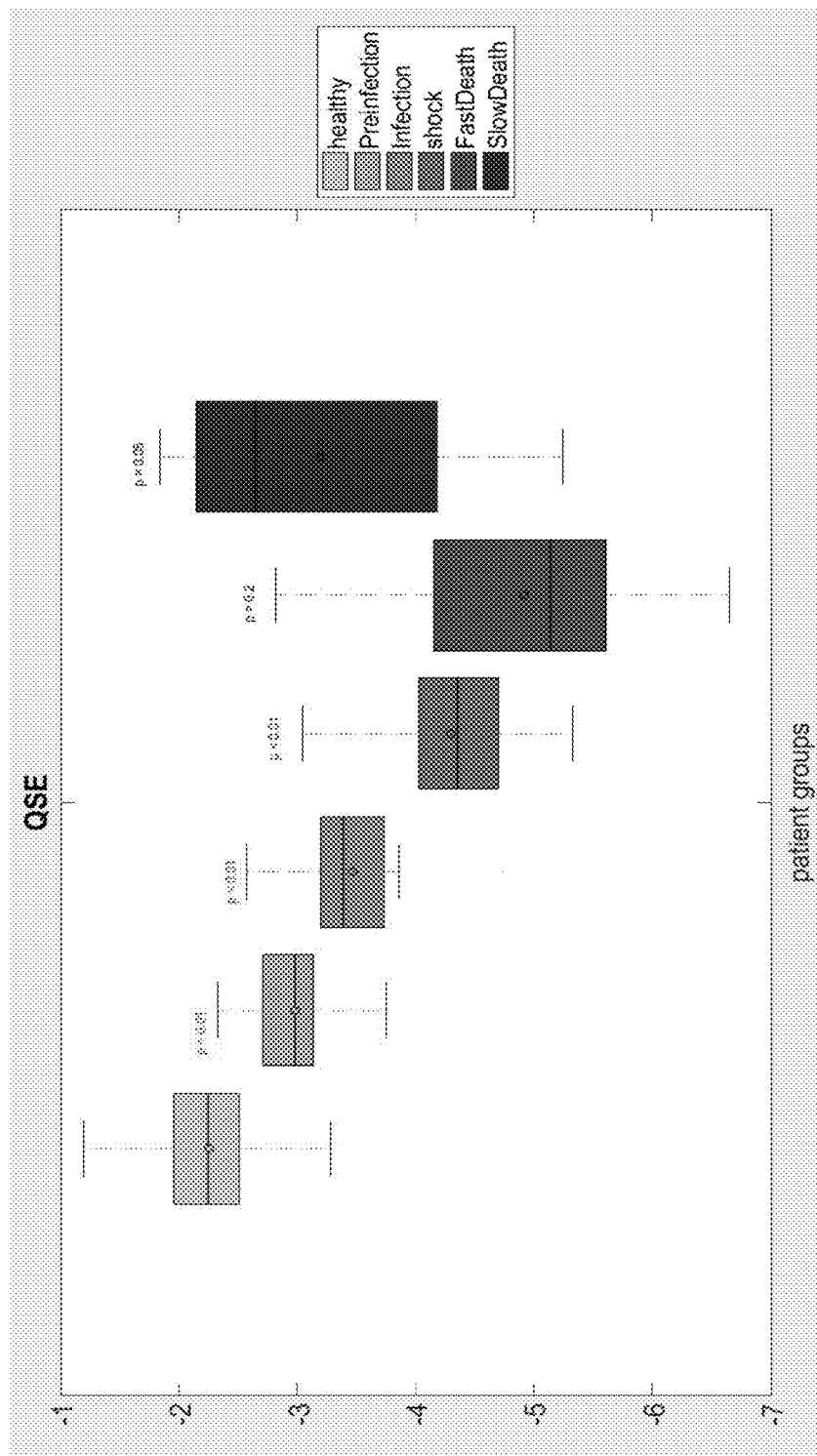
FIG. 5 is a chart illustrating quadratic sample entropy variability measures for a set of patient groups.

FIGS. 4 and 5 provide examples of two different variability measures (Coefficient of variability and Quadratic Sample Entropy (QSE)) for a number of different patient groups. Healthy=healthy volunteers (across all ages); Pre-infection=bone marrow transplant patients prior to infection; Infection=bone marrow transplant patients with an active infection; Shock=patients in the intensive care unit in septic shock; FastDeath=Patients (prior to withdrawal) who die within 2 hours of WLST; SlowDeath=Patients (prior to withdrawal) who take longer than 2 hours to die after WLST.

Figure 7:
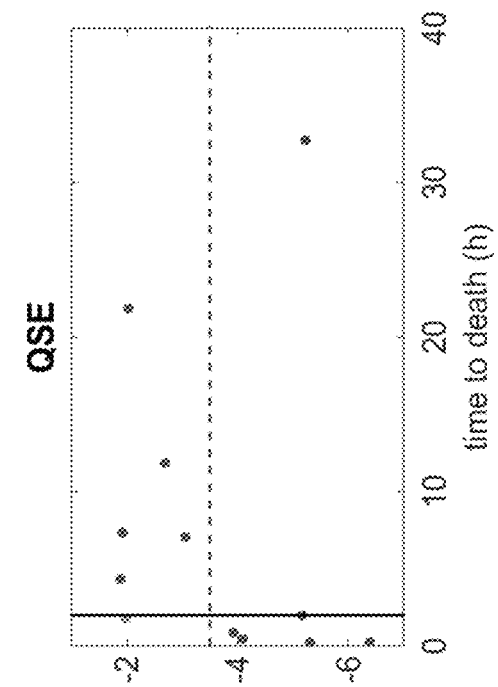
FIG. 7 illustrates classification using single heart rate variability measures using quadratic sample entropy.
Figure 6:
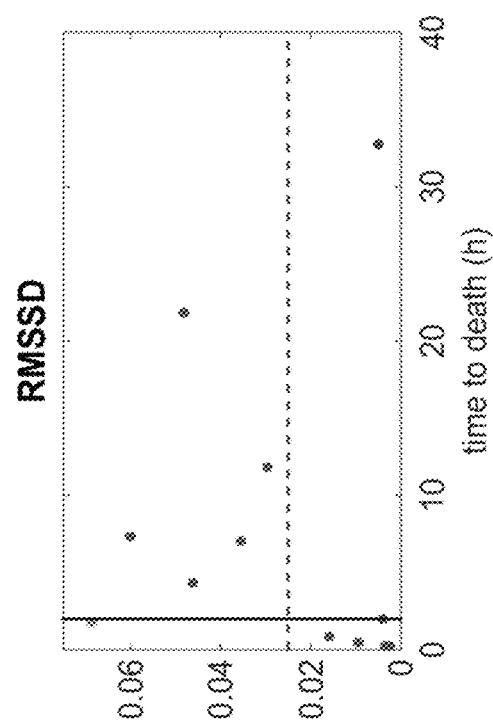
FIG. 6 illustrates classification using single heart rate variability measures using root mean sum of successive differences.

FIGS. 6 and 7 illustrate classification using single HRV measures. Plots of individual variability measures vs the time to death for each patient are shown: In FIG. 6: Root Mean Sum of Successive Differences (RMSSD), and in FIG. 7: Quadratic Sample Entropy (QSE). The black vertical line delineates the 2 hour mark (border of "fast" vs "slow"). The red dashed line indicates a potential HRV threshold that could be used to separate the two groups (for example, using a linear support vector machine). Green circle (top left in plot): patient given phenylephrine and norepinephrine 10 minutes prior to the HRV measurement window, resulting in an artificially high HRV value (false negative). Red circle (bottom right in plot): patient is given relatively large doses of morphine and midazolam 45 minutes prior to WLST, possibly resulting in lower HRV values (false positive). Each univariate classifier could correctly classify 10/12 patients (5/6 fast, 5/6 slow).

Figure 8:
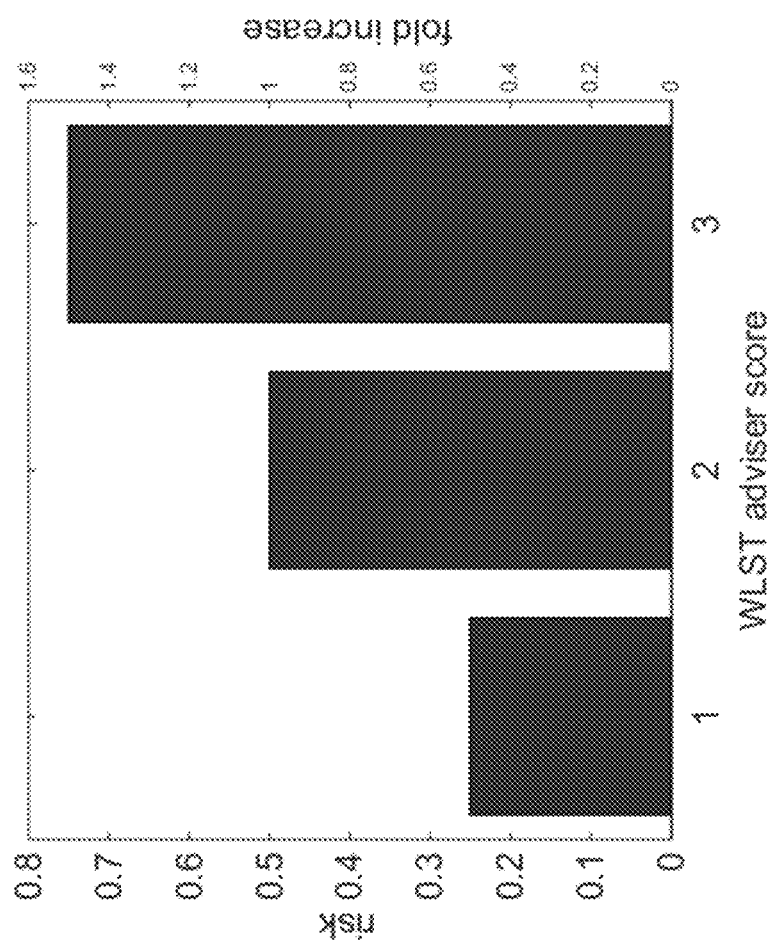
FIG. 8 provides an ensemble of logistic regression models employing several different variability measures for a set of patients.

FIG. 8 shows an ensemble of logistic regression models employing several different variability measures was built using data from 12 different patients (using leave-one-out cross-validation). The WLST adviser score was calculated using the average output of each logistic regression model. The population was split into three groups according to their WLST adviser score (lower tertile, middle tertile, and highest tertile). The risk for each group was calculated as the number of patients that die quickly within that group, divided by the total number of patients in that group. The fold increase in risk was calculated as the risk in that group divided by the risk of dying quickly over the entire dataset.

The variability measures can also be used as input features in prediction tools for other time points possibly of interest in a dying patient, such as the first time to a systolic or mean blood pressure less than Y mmHg, or an oxygen saturation value less than Z %. A combination of the estimates of the time to death and the time to a given value of blood pressure or oxygen saturation value could be of interest in creating estimates of the likelihood of a functional warm ischemic time being less than a certain threshold.

Statistical Model Identification

The measures of variability to be included in the statistical model, as well as the optimal thresholds used by the algorithms to separate between the fast and slow groups, are selected based on a repeated random sub-sampling cross-validation; in brief, an equal subset of the fast and slow populations are randomly extracted from the whole sample to train the model, and the rest of the data is used to test its performances; in particular, a Receiver Operating Characteristic (ROC) curve is extracted, and the ROC Area under the curve (AUC) is computed. The process is then repeated many times, e.g., 1000 times, each time training the statistical model with a subset of the data and testing it on the remaining data, thus creating a distribution of ROC AUC values. A greedy approach repeating the presented procedure is used to select the variability measures which constitute the ensemble maximizing the median ROC AUC.

Decision Support Indices Creation

Figure 9:
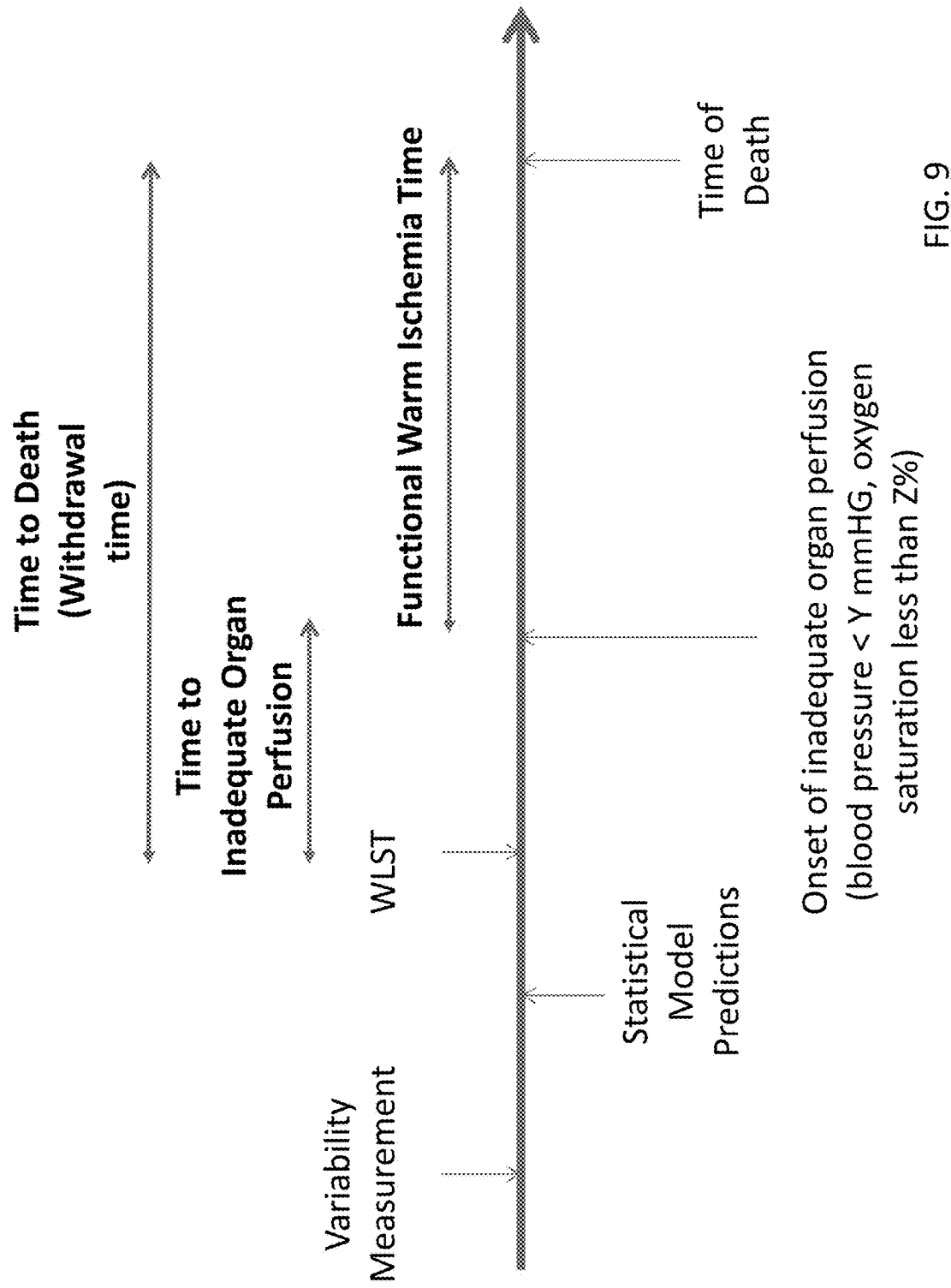
FIG. 9 is a timeline chart illustrating events associated with WLST.

The statistical model results in a score that can be used in multiple ways, depending on the targeted use. FIG. 9 illustrates the relative points in time and time periods mentioned below.

Estimate Risk of Death within a Given Period after WLST.

This index is evaluated prior to WLST (or shortly after if variability immediately after WLST is also included). The model output is transformed into the fold increase in risk of death by dividing it into ranges, and computing for each range the likelihood that a patient with that score dies within the given period of time after WLST.

Estimate the Probability of Time to Onset of Inadequate Organ Perfusion within a Given Period.

This index is evaluated prior to WLST (or shortly after if variability immediately after WLST is also included). The score can be transformed into the fold increase in risk of the blood pressure and/or oxygen saturation dropping below a given threshold, by dividing it into ranges, and computing for each range the likelihood that a patient with that score will have fallen below the blood pressure/oxygen saturation threshold within the given period of time after WLST (see, for example, FIG. 8).

Estimate the Probability that the Functional Warm Ischemic Time Will Remain Less than a Given Threshold.

This index is evaluated prior to WLST (or shortly after if variability immediately after WLST is also included). The score can also be transformed into the fold increase in risk that the functional warm ischemic time exceeds a given threshold, by dividing it in ranges, and computing for each range the likelihood that a patient with that score will have a functional warm ischemic time less than the given threshold.

Obtaining Variability Measures

As discussed above, the WLST decision analyzer 10 may be used in conjunction with individual variability measures and analyses to provide decision support indices, e.g. along with an output such as a report. As such, the generation of such decision support indices can be applied in any context in which variability measures, obtained from a variability analysis component 14', can be applied. For example, support indices can be generated using data obtained in real-time, previously obtained data, data obtained in an intensive care unit (ICU), data obtained using portable monitoring devices recording variability, etc. For example, data can be summarized in a mathematical model, which is then used for the computation of quality. A quality assessment of variability therefore is not dependent on any particular mechanism for obtaining the variability data, so long as a set of variability measures is available, and a quality measure can be obtained, as explained in greater detail below. The following illustrates three exemplary monitoring sites 111 (e.g., 111a, 111b, 111c) to demonstrate the various ways in which the variability measures can be obtained in order to generate a quality assessment. Further detail concerning an underlying software framework for obtaining and distributing variability data can be found in applicant's co-pending U.S. patent application Ser. No. 12/752,902, published under US 2010/0261977 and issued as U.S. Pat. No. 8,473,306 to Seely, the entire contents of which are incorporated herein by reference.

Figure 10:
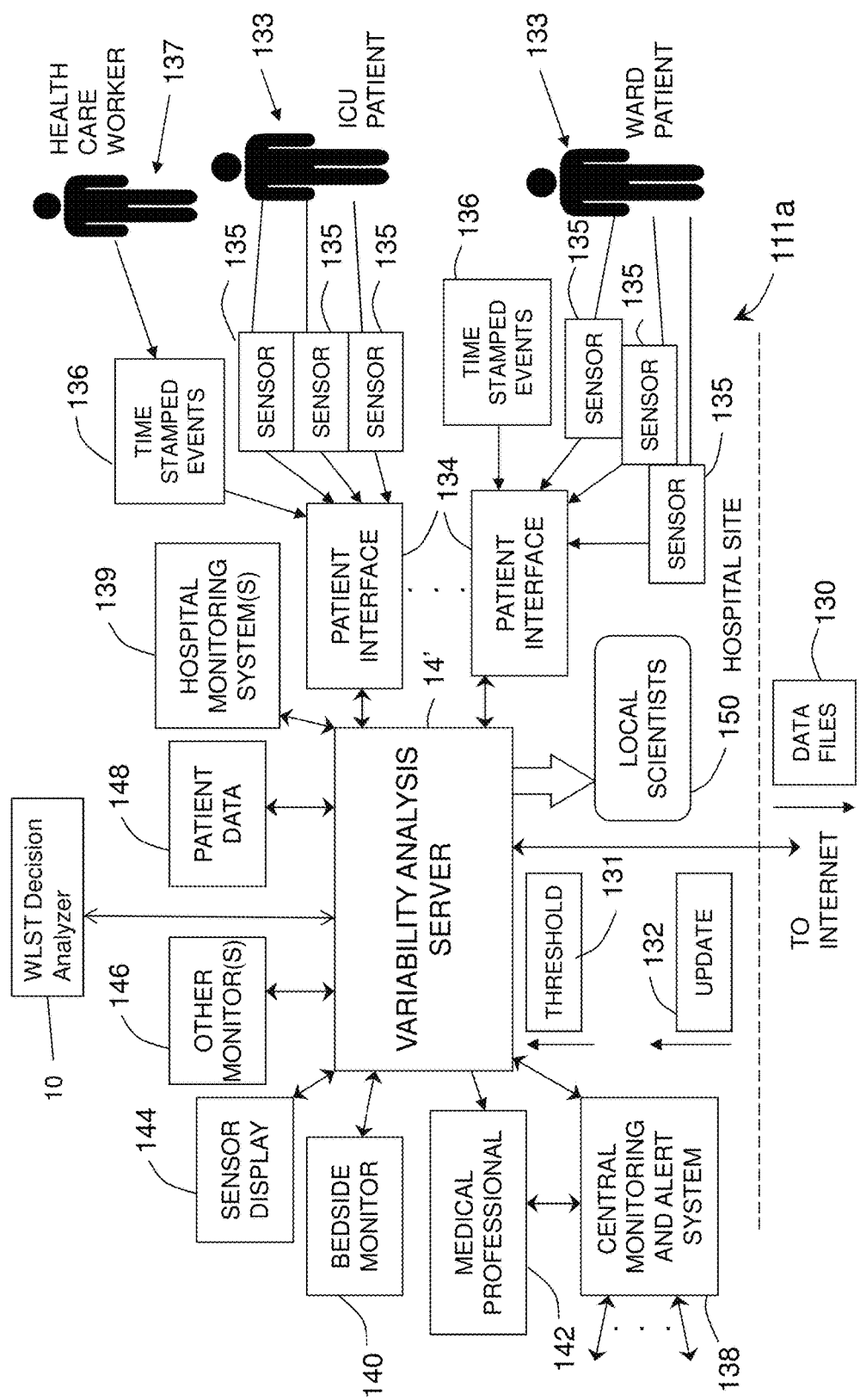
FIG. 10 is a block diagram of a hospital site including a variability analysis server having a quality module.

An example of a hospital monitoring site 111a is shown in FIG. 10. The elements shown in FIG. 10 are meant to illustrate several possible components that may interact with one another at the hospital site 111a, however, any number (or all) of these elements can be used or not used in specific hospital sites 111a depending on the actual equipment and/or personnel present at the hospital site 111a and the needs of the patients 133 and personnel. In addition, the parameters being monitored (and the monitors themselves) may differ from network to network. As will be explained, at each monitoring site 111, including the hospital site 111a shown in FIG. 10, is at least one variability analysis server 14' for using acquired data to conduct variability analyses over time and generate data files 130 that can be viewed at the site and provided to, for example, a central service (not shown). The variability analysis server 14' includes or otherwise has access to a WLST decision analyzer 10. As shown, each variability analysis server 14' can interface with multiple patients 133 and, as such, typically only one variability analysis server 14' is required at each monitoring site 111. The variability analysis server 14' gathers data acquired from one or more patients 133 through individual patient interfaces 134, computes the measures of variability (i.e. conducts variability analyses) for one or more patient parameters, and connects to, for example, a central server through the Internet, for facilitating the transfer and/or receipt of data files 130, threshold data 131 and update data 132. As shown, there can be different types of patients 133 such as those in the ICU or in a regular hospital ward.

The patient interfaces 134 monitor physiological parameters of the patient 133 using one or more sensors 135. The data or patient parameters can include any variable that can be accurately measured in real time or intermittently. The data may be obtained from a continuous waveform (at a certain frequency level, e.g. 100 Hz for a $CO_2$ capnograph or 500 Hz for an EKG), or taken as absolute measurements at certain intervals, e.g. temperature measurements. The sensors 135 and patient interfaces 134 may include, for example, an electrocardiogram (ECG), a $CO_2$ capnograph, a temperature sensor, a proportional assist ventilator, an optoelectronic plethymography, a urometer, a pulmonary arterial catheter, an arterial line, an $O_2$ saturation device and others. To provide more meaning to the data acquired through the sensors 135, clinical events are associated with the data, through an act of recording time stamped events 136, which are typically entered by a heath care worker 137 in the hospital (bedside) environment. Clinical (time stamped) events can be physical activity, administration of medication, diagnoses, life support, washing, rolling over, blood aspiration etc. The clinical events are associated with a specific time, which is then also associated with the data that is acquired at the same specific time using the sensors 135. It will be appreciated that the clinical events can also be recorded in an automated fashion, e.g. by utilizing algorithms which detect events electronically and process such events to designate them as clinical events or noise. In this example, the patient interface 134 is configured to gather the time stamped event data 136 concurrently with the sensor data 135, further detail being provided below. It may be noted that additional non-time-stamped information (e.g. demographics) can also be recorded for each patient.

As can be seen in FIG. 10, the variability analysis server 14' not only connects to the patient interfaces 134 and the Internet, but also to several other components/entities within the hospital site 111a. For example, the server 14' can interface with a hospital monitoring system 139 such as a nurse's station, as well as a central monitoring and alert system 138. The central monitoring and alert system 138 is capable of monitoring the variability analyses performed by the variability analysis server 14' in order to detect critical or potentially critical situations evident from such variability analyses and provide an alert or alerts to a medical professional 142, who can also receive data directly from the variability analysis server 14'. The variability analysis server 14' can be embodied as a fixed unit or a moveable unit such as on a cart, in order to facilitate movement about the hospital site 111a to serve multiple patients 133 in multiple locations. Similarly, the variability analysis server 14' can be a proprietary apparatus or can be embodied as an add-on to existing beside or centralized equipment to minimize space.

The variability analysis server 14' can also interact with a bedside monitor 140, which may be made available to or otherwise represent a nurse or other personnel that monitors the patient 133 at the bedside. Similarly, the variability analysis server 14' can also interact with sensor displays 144, which are associated with other medical equipment such as ECGs, blood pressure sensors, temperature sensors etc. As noted above, the variability analysis server 14' can be a separate, stand-alone unit but may also be integrated as a plug-in or additional module that in this case could be used or integrated with existing bedside monitoring equipment, displays and sensors. FIG. 10 also shows other monitors 146 which can include any other monitoring system or equipment that either can provide useful medical data or patient data 148 or would benefit from the data acquired by the variability analysis server 14'. Patient data 148, e.g. provided by an electronic patient database (not shown) or manually entered can also interact with the variability analysis server 14'. As will be discussed below, the patient data 148 may be appended to, or included with the data files 130 to provide further context for the data contained therein. This enables patient specifics such as age, general health, sex etc. be linked to the acquired data to assist in organizing data into demographics. As also shown in FIG. 10, the variability analysis server 14' can provide data or otherwise useful information for local scientists 150 that are interested in or involved in the implications and effects of variability. It will be appreciated that patient privacy and other concerns can be addressed as required, by adding data security or other de-identification measures.

Figure 11:
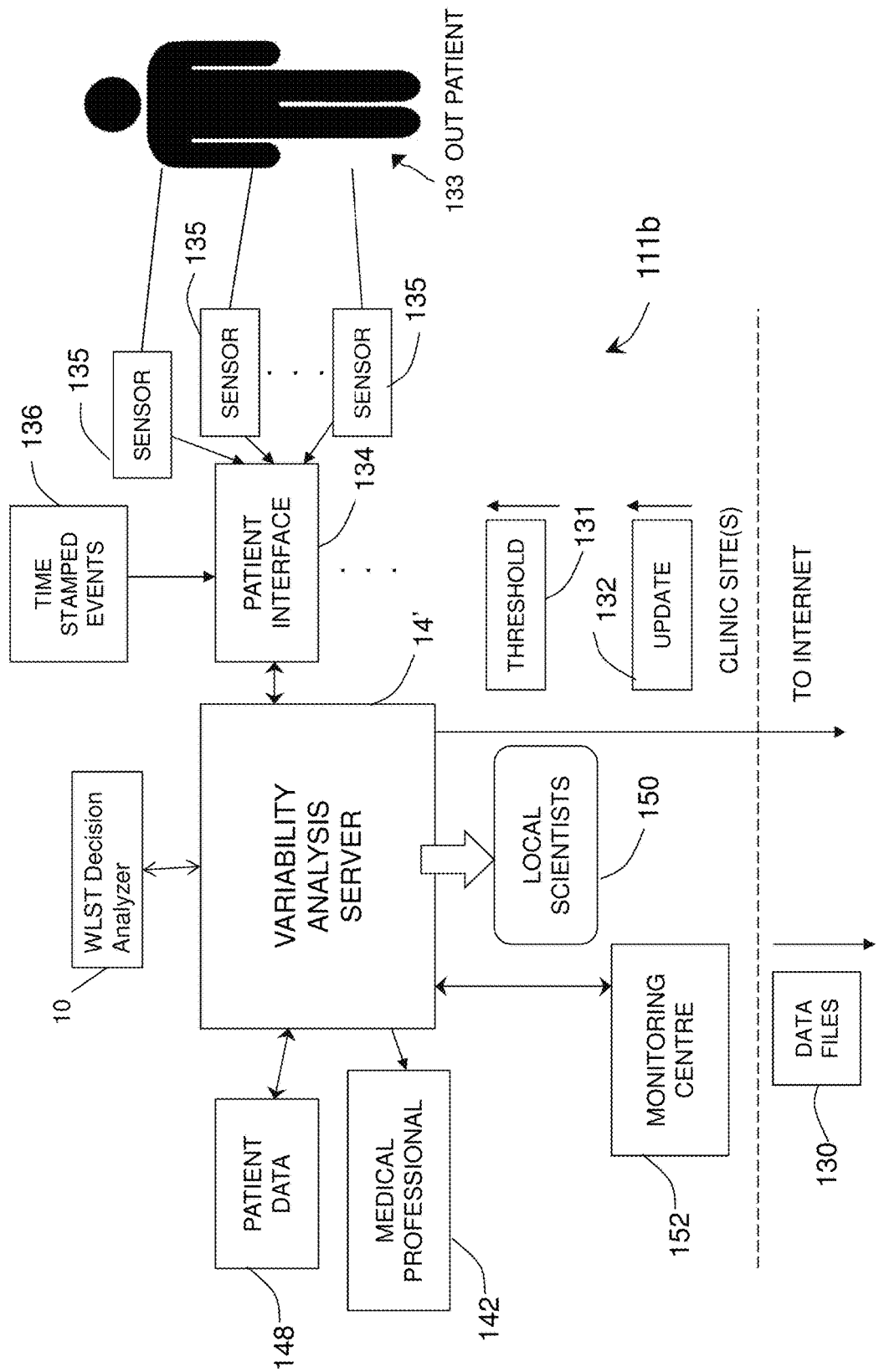
FIG. 11 is a block diagram of a clinic site including a variability analysis server having a quality module.

Turning now to FIG. 11, a clinic site 111b is shown. An example of a clinic site 111b is a bone marrow transplant clinic. Similar to the hospital site 111a discussed above, the clinic site 111b includes a variability analysis server 14', that obtains data from one or more patient interfaces 134, and connects to the Internet for facilitating data transfer (i.e. to send data files 130 and to receive threshold data 131 and update data 132). In the clinic site 111b, the patients 133 are referred to as outpatients as they are not admitted to a hospital. The sensors 135, clinical events recorded as time stamped events 136 and patient data 148 is acquired and used in a manner similar to that discussed above and thus further details need not be reiterated. Similarly, the variability analysis server 14' can provide data and interact with medical professionals 142 at the clinic site 111b, as well as local scientists 150, if applicable. The clinic site 111b may include one or more variability analysis servers 14', and would typically include a monitoring center 152 that monitors the analyses of the various outpatients 133 and provides alerts if necessary. The monitoring center 152 enables the clinic's variability analysis server 14' to be monitored from a remote location and allows personnel to monitor several servers 14' if several are present in the clinic. In this way, a central monitoring center 152 can be used to service several clinic sites 111b.

Figure 12:
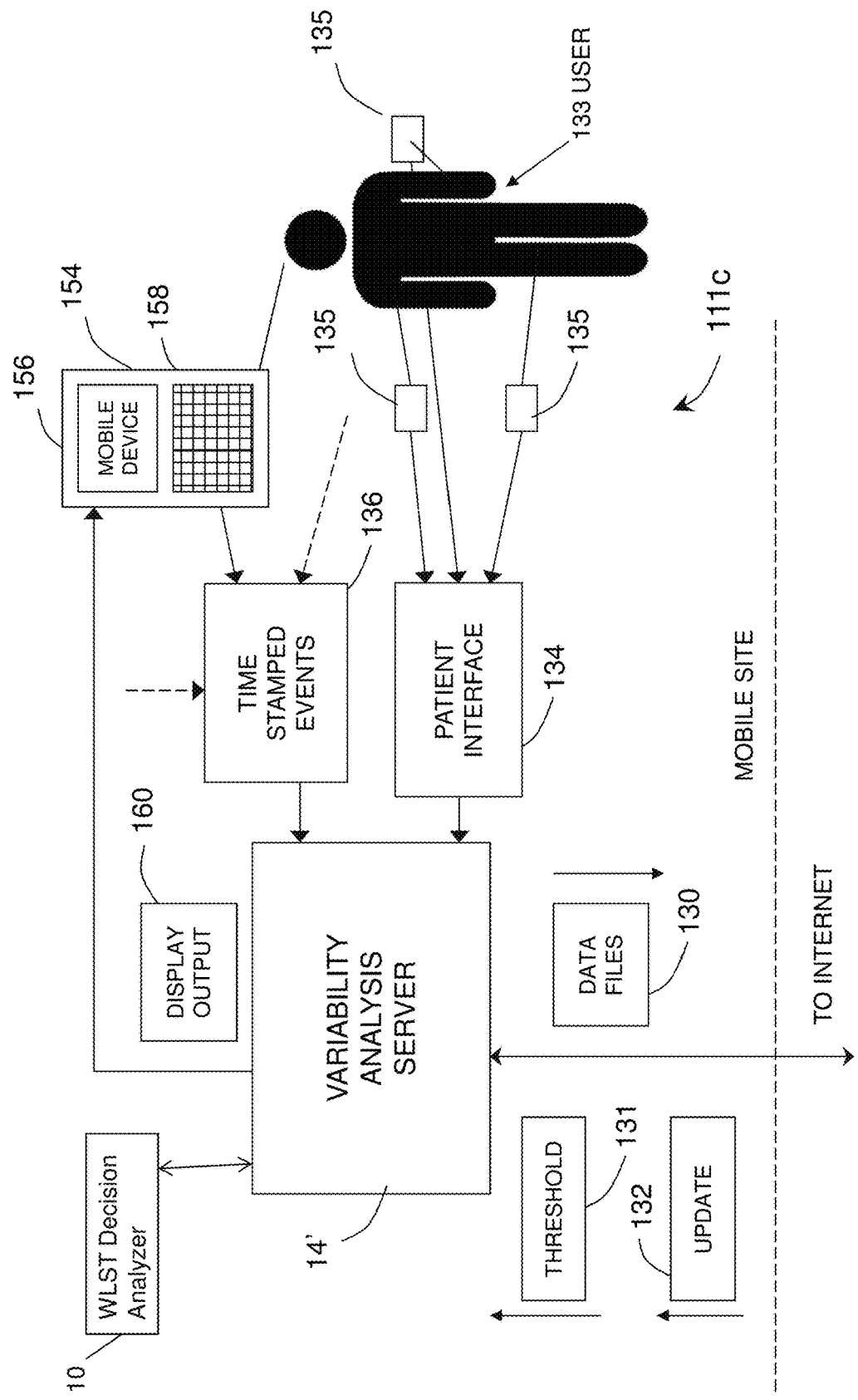
FIG. 12 is a block diagram of a mobile site including a variability analysis server having a quality module.

A mobile site 111c is shown in FIG. 12. The mobile site 111c enables the capabilities of the variability analysis server 14' to be used outside of the hospital and clinical environments and, as such, in this embodiment, the mobile site 111c serves any "user" or "subject". For the sake of consistency, hereinafter the term "patient" will refer collectively to any user or subject. In this way, it may be appreciated that variability analyses can be performed on any user, including athletes, firefighters, police officers, or any other person that can benefit from monitoring variability of one or more physiological parameters. This can therefore extend to providing real-time monitoring in extreme environments such as during a fire, in a mine, during rescue missions etc. where variability can indicate a potentially critical situation. In all cases, variability can be monitored over time and analyzed on an individual basis for any patient 133 such that the resultant data is specific to that individual. Using the wider system allows a central service to take advantage of the individual results for many patients 133 and ascertain further and more complete information. The mobile site 111c generally represents any site that includes a variability analysis server 14', which connects to the system 8 and can communicate with one or more patients 133, whether they are patients in the traditional sense or another type of user.

In the example shown in FIG. 12, the user 133 generally includes a mobile device 154 and has a number of sensors 135 that are in communication with a variability analysis server 14'. The mobile device 154 can also be used to provide inputs, e.g. for the time stamped event data 136, as well as to provide a display to the user 133 for entering parameters or to view display data 160 acquired by the sensors 135 and/or processed by the server 14'. The connections between the mobile device 154 and the server 14', as well as between the sensors 135 and patient interface 134 can be wired or wireless and the variability analysis server 14' can be a fixed unit at a base station or a portable unit such as on a cart at a monitoring center. The mobile device 154 can be a personal digital assistant (PDA) or smartphone, mobile telephone, laptop computer, tablet computer, personal computer, or any other device that can provide an input device, a display and some form of connectivity for interacting with the variability analysis server 14', preferably in a completely mobile manner.

As noted above, each monitoring site 111 may include a variability analysis server 14'. Details of various embodiments of existing variability analysis apparatus and configurations can be found in U.S. Reissue Pat. No. RE41,236 E to Seely, the entire contents of which are incorporated herein by reference.

Variability Quality

Physiological waveforms are now harvested at the bedside and manipulated to provide informational and decisional data points for clinicians and caregivers. For example, the study of heart rate variability (HRV) which is derived from the electrocardiogram (ECG) has benefited from nearly two decades of research and its applications in clinical practice are wide ranging. HRV is widely studied and used as a marker of illness severity.

Variability analysis measures the complexity of a time series of event occurrences, such as heart beats or breaths. As discussed above, assessing the quality of the events, and the underlying waveform from which the events are derived is important to validate the subsequent interpretation of the variability measurements. The quality of the variability measurements themselves is also important in providing confidence in the reported values.

Figure 13:
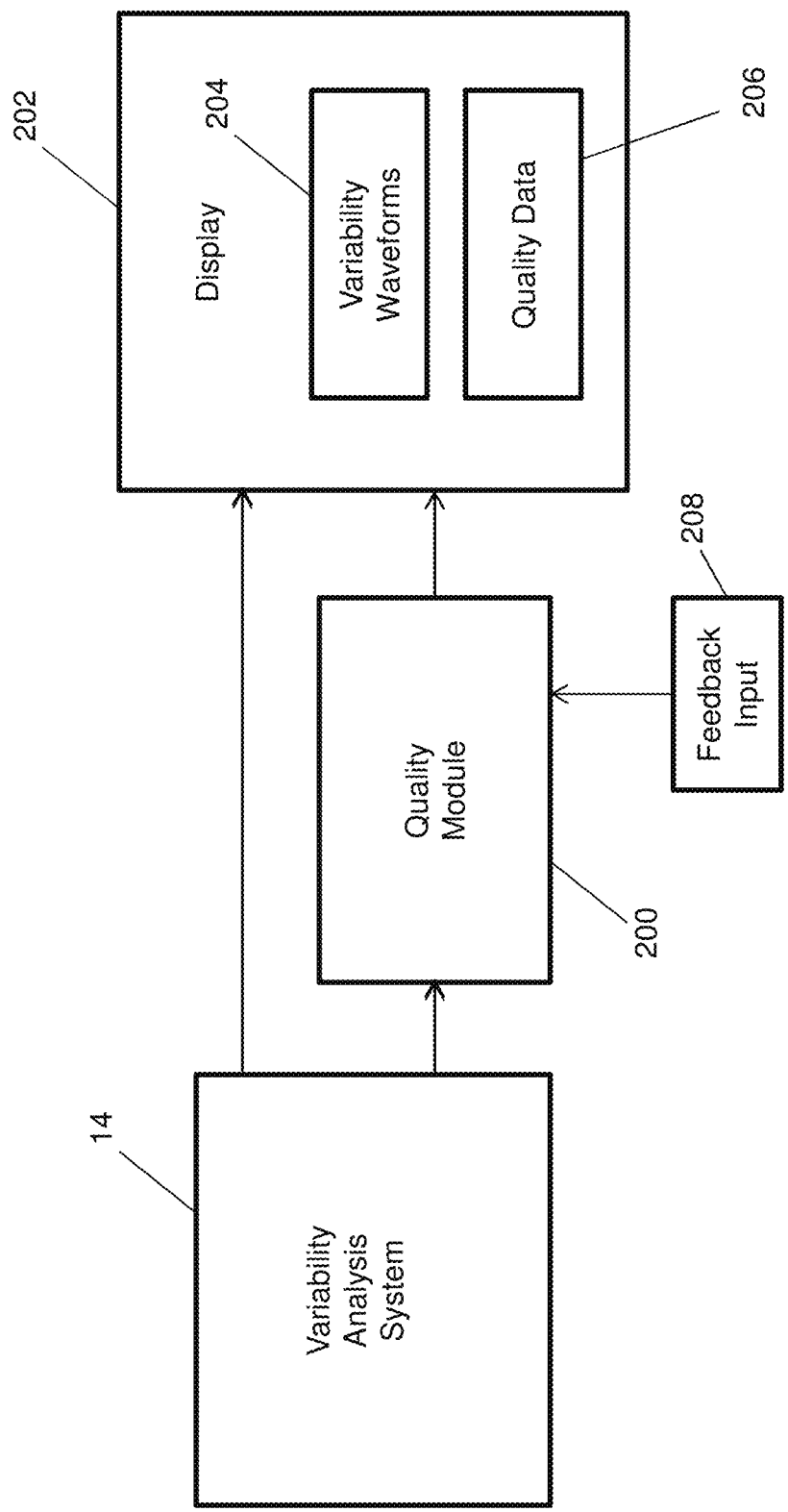
FIG. 13 is a block diagram illustrating the incorporation of quality measurements into a variability analysis.

FIG. 13 illustrates a variability monitoring/analysis environment in which a quality module 2000 is incorporated into or otherwise coupled to or integrated with a variability analysis system 14. Through this integration with the variability analysis system 14, the quality module 200 can generate quality data 206 (e.g., reports, measures, etc.) that can be displayed along with variability waveforms 204 on a display 202 of a computing system. For example, such a quality analysis can be performed in conjunction with a variability analysis performed in connection with an extubation decision support process as described above.

The quality module 200 may also be configured, as shown in FIG. 13, to receive feedback input 208, such as user assessments of the quality of a particular variability waveform, interval or individual measurement, which can enhance the quality data 206.

It can be appreciated that the components in FIG. 13 are shown in isolation for illustrative purposes only and such components may be configured in different arrangements. For example, the components shown in FIG. 13 may be integrated into a single computing device or may operate within a distributed or otherwise networked system, and may also be further integrated with a WLST decision analyzer 10.

The present quality assessment therefore includes a modular framework for the analysis of a generic physiological waveform, and may also include event and stationarity assessments to prepare a high quality event time series for a variability analysis, and to measure the quality of the reported variability measures. The overall quality of the window can be reported as an index which summarizes the quality of the data at each step in processing. The framework described herein is also applied to the capnogram which is one embodiment of the method.

Figure 14:
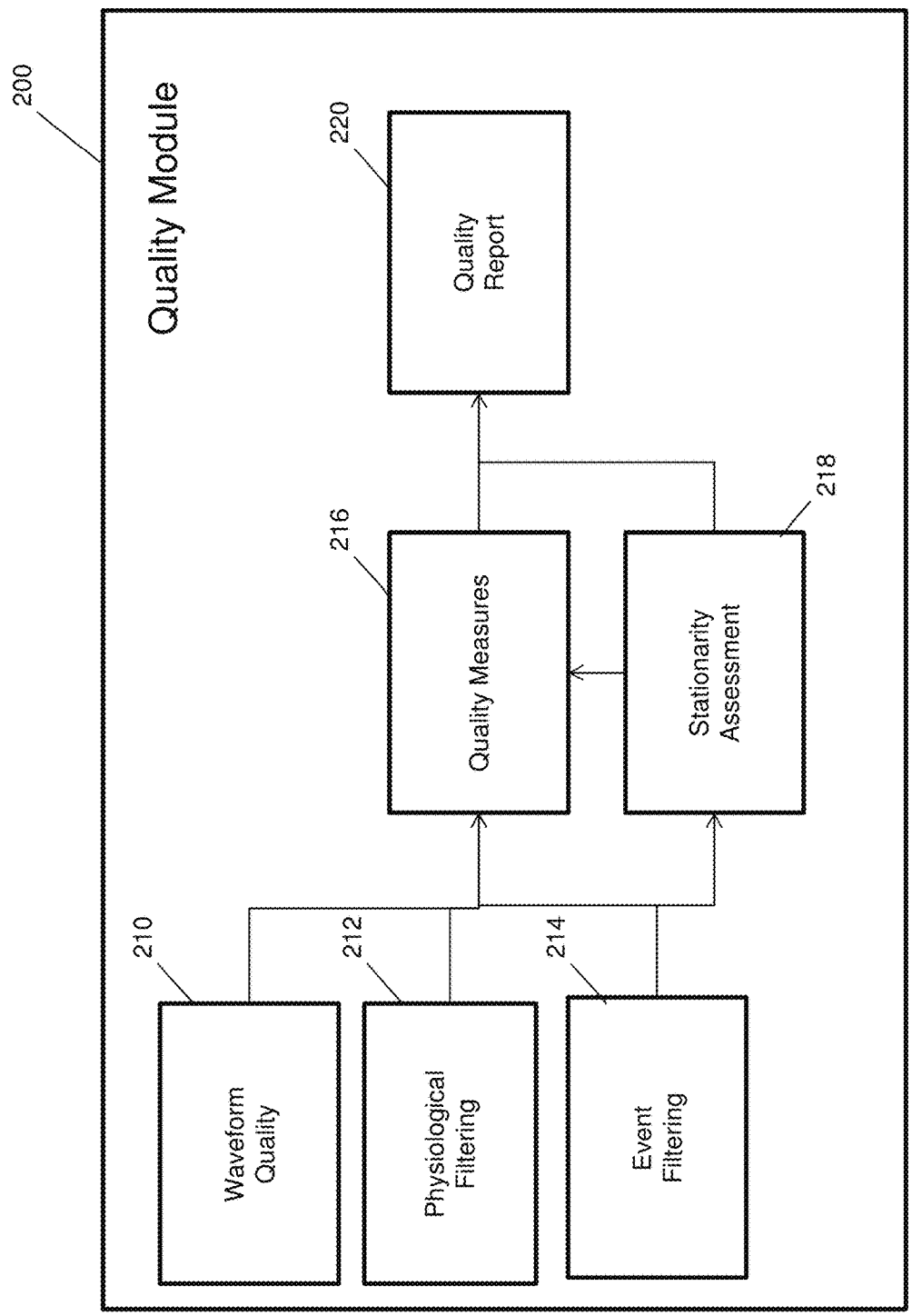
FIG. 14 is a flow diagram illustrating a process for quality assessment.

FIG. 14 illustrates further detail of a configuration for the quality module 200. In the example shown in FIG. 14, the quality module 200 performs a waveform quality stage 210, a physiological filtering stage 212, and an event filtering stage 214, all of which feed into a stationarity assessment 218 and a quality measures stage 216. The quality measures and stationarity assessments are then fed into a quality report stage 220, which reports on the quality of the variability waveforms being displayed, to enhance the data conveyed by such waveforms.

The following provides a quality assessment, addressing specific concerns for variability analysis. One embodiment uses the end tidal CO2 signal as an input waveform presented in section III.

The quality stages shown in FIG. 14 may be specifically designed for the purpose of variability analysis conducted over time as is its application to the capnogram signal. These quality stages can be used to ensure events used for variability calculations are of high quality and exhibit stationary behavior over a suitable period of time. The quality stages can be used to estimate the quality of the signal (i.e. level of noise and artifacts such as disconnections, saturation, baseline wandering, motion artifacts, etc.), and to exclude from the analysis segments of the signal that are of poor quality (thereby not enabling a proper computation of the event time series). A particular concern of stationarity which is assessed in the stationarity assessment stage 218, and which is of great importance for variability, is also addressed with these quality stages. It may be noted that in its simplest form, stationarity is the property of having stable statistical moments. It is recognized as a requirement for many popular techniques of time series analysis, including complexity of the variability measures. Without stationarity, interpreting the measures with confidence may be challenging (see R. Manuca and R. Savit, "Stationarity and nonstationarity in time series analysis," *Physica D*, vol. 99, pp. 134-161, 12/15. 1996).

In a variability analysis, variability is calculated over time on the high quality event time series, usually on a plurality of windows, which may overlap. A quality assessment for variability may also be provided for variability measures calculated in time periods surrounding a clinical event. Therefore combining the waveform and event quality measures over a window provides a more complete quality assessment. The diagram of the assessment is presented in FIG. 10, and a detailed representative diagram for the quality assessment as it is integrated with the variability analysis, is presented in FIG. 15. In FIG. 14, as noted above, the processing stages include assessing the quality of the input waveform to identify segments which are suitable for segmentation into events. Following the segmentation into events, these events are stratified into three categories: non-physiological event, physiological events, and high quality events. Multiple methods for this stratification are described in section II.

Figure 15:
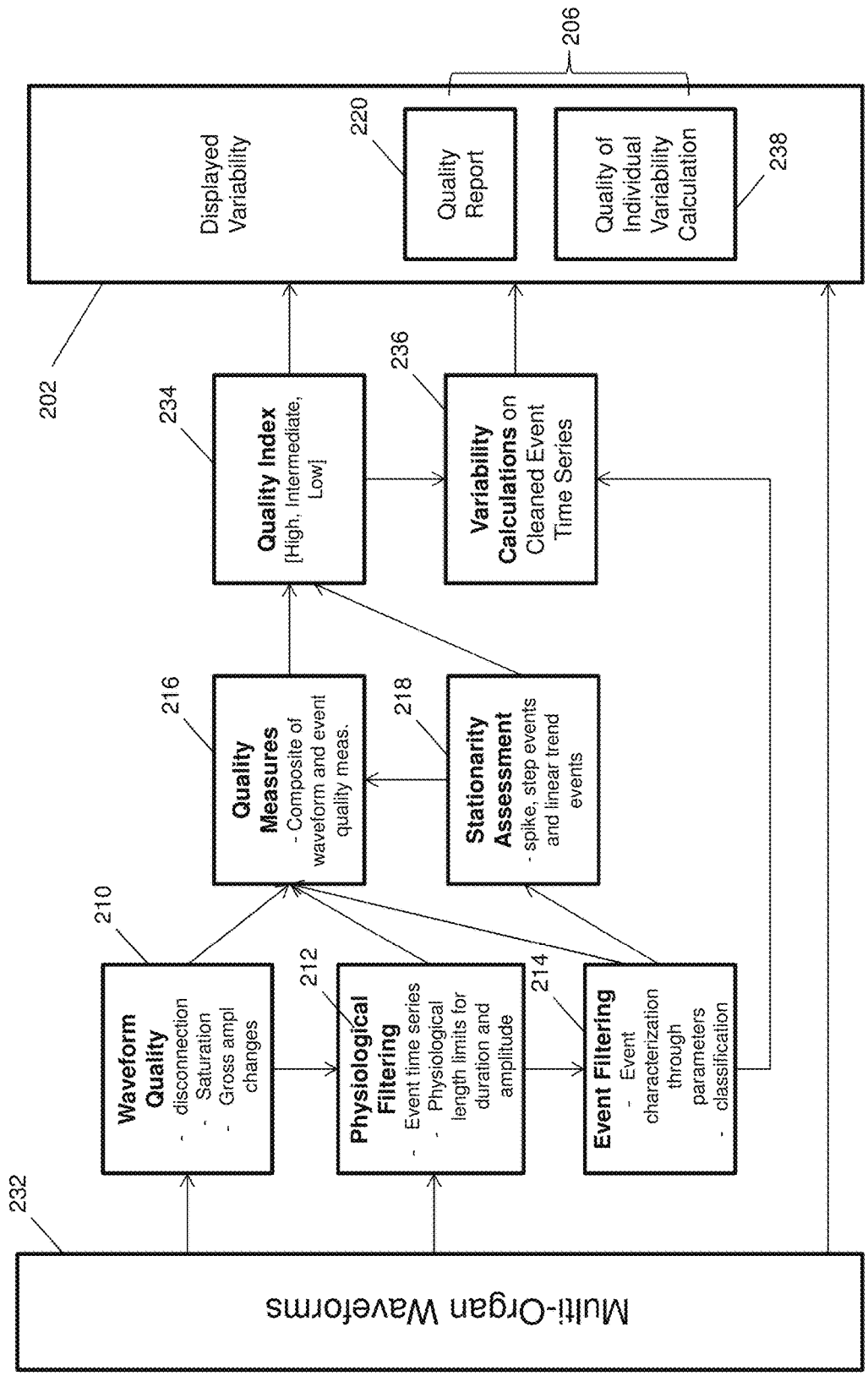
FIG. 15 is a representative diagram of quality framework for variability quality assessment.

As illustrated in FIG. 15, using time intervals (windows), the high quality event time series is assessed for stationarity in the stationarity assessment stage 218. The stationarity assessment stage 218 has been found to be important for variability measurements. Data obtained from the initial processing stages (waveform quality stage 210, physiological filtering stage 212, event filtering stage 214, and stationary assessment stage 218) are used to create quality measures in the quality measures stage 216. The quality measures are related to both a window (or interval) and to the individual variability measurements within that window. The quality measures may be implemented using a machine learning model (e.g. using neural networks, etc.) to optimally combine waveform, event, physiological and stationarity information. These measures provide information to the clinician about the underlying waveform and event time series, and about the quality of the measurements; providing confidence about the interpretation. Measurements from low quality windows (e.g., low quality because of the waveform, event, stationarity or variability) may be chosen not to be displayed (either graphically or numerically). This assures clinicians that displayed information is at least of intermediate quality.

The quality index 234 is implemented optimally combining the quality measures and the stationarity information using a machine learning model (e.g. using decision trees). The quality index 234 is used to summarize the information from the quality measures into a simple metric which can be used by those clinicians uninterested in the finer details of the quality analysis. The quality report 220, derived from the quality assessment is linked, through a time stamp to the waveform, event and variability information and displayed on the display 202. In addition to the quality report 220, the quality of individual variability calculations 238 can also be displayed as shown in FIG. 15. If one variability measurement is selected on the display 202, the quality report 220 shown for that window can be used to call the waveform and event time series for that window. Similarly, selection of individual measures of variability can cause individual quality measures to be displayed. The physiological filtering 212 and event filtering 214 stages are used to annotate each event in that time series as one of the three categories mentioned above, allowing the clinicians to inspect the waveform and event annotations. The number of quality levels and threshold values on the quality measure to create is modular and can be changed for specific applications. For example, different stationarity requirements could be enforced for certain input types of event time series.

It can be appreciated that the framework described herein may be applied to any physiological waveforms including sets of multi organ waveforms such as the ECG and capnography waveforms which are produced by different organ systems yet are intrinsically related as measure by the cardiopulmonary synchrony (P. Z. Zhang, W. N. Tapp, S. S. Reisman and B. H. Natelson, "Respiration response curve analysis of heart rate variability," *IEEE Transactions on Biomedical Engineering*, vol. 44, pp. 321, April 1997). Amongst the two signals, only the ECG has a clearly defined physiological model and morphology and has been extensively studied (Electrophysiology, Task Force of the European Society of Cardiology the North American Society of Pacing, "Heart Rate Variability Standards of Measurement, Physiological Interpretation, and Clinical Use," *Circulation*, vol. 93, pp. 1043-1065, March 1996), and (S. Cerutti, A. L. Goldberger and Y. Yamamoto, "Recent Advances in Heart Rate Variability Signal Processing and Interpretation," *IEEE Transactions on Biomedical Engineering*, vol. 53, pp. 1, January 2006).

The capnogram has benefited from extensive documentation of tracings (B. Smalhout and Z. Kalenda, *An Atlas of Capnography.*, 2nd ed. The Netherlands: Kerckebosche Zeist, 1981). Prior to the widespread use of powerful computers, analysis and measurements were done by hand (measuring angles, visual inspection of shape, and selection of individual breaths for classifiers and detectors), see (B. Smalhout and Z. Kalenda, *An Atlas of Capnography.*, 2nd ed. The Netherlands: Kerckebosche Zeist, 1981), and see (J. M. Goldman and B. H. Dietrich, "Neural network analysis of physiologic waveforms," in *Proceedings of the Annual International Conference of the IEEE Engineering in Medicine and Biology Society*, Vol. 13, 1991, pp. 1660).

Limitations of this method may include reproducibility, a reliance on experts with limited availability, and a limit to the number of analyses which may be conducted. To overcome this, the system described herein extends the knowledge gained from HRV and address the limitations in traditional capnograph processing to provide a complete quality assessment for generic physiological waveform inputs. The quality of the signal is ascertained at multiple levels of processing (waveform, events, stationarity), which are specific to variability analysis. The quality process applied to the end tidal $CO_2$ signal as an example of use in section III, and an example of quality report on the ECG is presented in section IV.

For simplicity and clarity of illustration, where considered appropriate, reference numerals may be repeated among the figures to indicate corresponding or analogous elements. In addition, numerous specific details are set forth in order to provide a thorough understanding of the examples described herein. However, it will be understood by those of ordinary skill in the art that the examples described herein may be practiced without these specific details. In other instances, well-known methods, procedures and components have not been described in detail so as not to obscure the examples described herein. Also, the description is not to be considered as limiting the scope of the examples described herein.

It will be appreciated that the examples and corresponding diagrams used herein are for illustrative purposes only. Different configurations and terminology can be used without departing from the principles expressed herein. For instance, components and modules can be added, deleted, modified, or arranged with differing connections without departing from these principles.

It will also be appreciated that any module or component exemplified herein that executes instructions may include or otherwise have access to computer readable media such as storage media, computer storage media, or data storage devices (removable and/or non-removable) such as, for example, magnetic disks, optical disks, or tape. Computer storage media may include volatile and non-volatile, removable and non-removable media implemented in any method or technology for storage of information, such as computer readable instructions, data structures, program modules, or other data. Examples of computer storage media include RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which can be used to store the desired information and which can be accessed by an application, module, or both. Any such computer storage media may be part of the system 8, any component of or related to the system 8, etc., or accessible or connectable thereto. Any application or module herein described may be implemented using computer readable/executable instructions that may be stored or otherwise held by such computer readable media.

The steps or operations in the flow charts and diagrams described herein are just for example. There may be many variations to these steps or operations without departing from the principles discussed above. For instance, the steps may be performed in a differing order, or steps may be added, deleted, or modified.

Although the above principles have been described with reference to certain specific examples, various modifications thereof will be apparent to those skilled in the art as outlined in the appended claims.

The invention claimed is:

1. A computer-implemented method of assisting decisions associated with events relative to withdrawal of life sustaining therapy (WLST), the method comprising:

accessing a waveform dataset to obtain waveform data previously collected from a plurality of patients just prior to or immediately after WLST;

obtaining from one or more variability analyzers, waveform data and a plurality of variability metrics in a variability data set comprising at least one measure of variability from one or more organ systems, each measure of variability comprising a computation of variability for a plurality of time intervals for a respective patient parameter, each measure of variability being indicative of a degree and character to which the respective patient parameter changes over an interval of time to enable changes in variability of the respective patient parameter to be observed over a period of time;

using the waveform dataset and the at least one measure of variability in the variability dataset to generate at least one predictive statistical model that predicts or provides a probability of an event relative to the WLST; and displaying via a user interface and/or outputting via a report, a clinical decision support indicator determined from the at least one predictive statistical model that is indicative of the event, wherein the displaying is performed in a clinical location where the WLST is performed to assist in a clinical decision related to the event.

2. The method of claim 1, wherein the indicator is associated with a risk of death within a given time from after WLST.

3. The method of claim 1, wherein the indicator is associated with a probability or likelihood of death within a given time frame after WLST, reflecting a functional warm ischemic time of the patient's organs.

4. The method of claim 1, wherein the statistical model is based on variability measures used to estimate a probability of time of death within a given time frame after WLST.

5. The method of claim 1, wherein the statistical model is based on variability measures used to classify a patient as likely to die or not to die within a given time frame.

6. The method of claim 1, wherein the clinical decision support indicator is provided to a decision support system based on variability measures to provide feedback on a likelihood that a given patient will die within a given time frame after WLST.

7. The method of claim 1, further comprising determining clinical information to be used in generating the statistical model.

8. The method of claim 1, further comprising enabling selection of the statistical model from one or more defined models.

9. The method of claim 1, further comprising performing data preprocessing on a received data set prior to extracting the variability data.

10. The method of claim 1, further comprising generating a report comprising an index based on the clinical decision support indicator.

11. A non-transitory computer readable medium comprising computer executable instructions for assisting decisions associated with events relative to withdrawal of life sustaining therapy (WLST), the non-transitory computer readable medium comprising instructions for:

accessing a waveform dataset to obtain waveform data previously collected from a plurality of patients just prior to or immediately after WLST;

obtaining from one or more variability analyzers, waveform data and a plurality of variability metrics in a variability data set comprising at least one measure of variability from one or more organ systems, each measure of variability comprising a computation of variability for a plurality of time intervals for a respective patient parameter, each measure of variability being indicative of a degree and character to which the respective patient parameter changes over an interval of time to enable changes in variability of the respective patient parameter to be observed over a period of time;

using the waveform dataset and the at least one measure of variability in the variability dataset to generate at least one predictive statistical model that predicts or provides a probability of an event relative to the WLST; and displaying via a user interface and/or outputting via a report, a clinical decision support indicator determined from the at least one predictive statistical model that is indicative of the event, wherein the displaying is performed in a clinical location where the WLST is performed to assist in a clinical decision related to the event.

12. The non-transitory computer readable medium of claim 11, wherein the indicator is associated with a risk of death within a given time from after WLST.

13. The non-transitory computer readable medium of claim 11, wherein the indicator is associated with a probability or likelihood of death within a given time frame after WLST, reflecting a functional warm ischemic time of the patient's organs.

14. The non-transitory computer readable medium of claim 11, wherein the statistical model is based on variability measures used to estimate a probability of time of death within a given time frame after WLST.

15. The non-transitory computer readable medium of claim 11, wherein the statistical model is based on variability measures used to classify a patient as likely to die or not to die within a given time frame.

16. The non-transitory computer readable medium of claim 11, wherein the clinical decision support indicator is provided to a decision support system based on variability measures to provide feedback on a likelihood that a given patient will die within a given time frame after WLST.

17. The non-transitory computer readable medium of claim 11, further comprising determining clinical information to be used in generating the statistical model.

18. The non-transitory computer readable medium of claim 11, further comprising enabling selection of the statistical model from one or more defined models.

19. The non-transitory computer readable medium of claim 11, further comprising performing data preprocessing on a received data set prior to extracting the variability data.

20. The non-transitory computer readable medium of claim 11, further comprising generating a report comprising an index based on the clinical decision support indicator.

* * * * *